United States Patent
Iorio

(10) Patent No.: US 10,532,869 B2
(45) Date of Patent: Jan. 14, 2020

(54) DEVICE FOR DETERRING ABUSE OF DRUGS

(71) Applicant: Eighty Eight Pharma, Inc., Foxboro, MA (US)

(72) Inventor: Matthew Iorio, Foxboro, MA (US)

(73) Assignee: EIGHTY EIGHT PHARMA, INC., Mansfield, MA (US)

( * ) Notice: Subject to any disclaimer, the term of this patent is extended or adjusted under 35 U.S.C. 154(b) by 160 days.

(21) Appl. No.: 15/821,538

(22) Filed: Nov. 22, 2017

(65) Prior Publication Data

US 2019/0127134 A1    May 2, 2019

Related U.S. Application Data

(63) Continuation-in-part of application No. 15/800,469, filed on Nov. 1, 2017, now abandoned.

(51) Int. Cl.
*B65D 77/04* (2006.01)
*A61M 39/10* (2006.01)
(Continued)

(52) U.S. Cl.
CPC ....... *B65D 77/0493* (2013.01); *A61M 5/5086* (2013.01); *A61M 39/1011* (2013.01); *B65D 51/002* (2013.01); *B65D 51/22* (2013.01)

(58) Field of Classification Search
CPC ............ A61M 39/1011; A61M 5/5086; B65D 51/002; B65D 51/22; B65D 77/0493;
(Continued)

(56) References Cited

U.S. PATENT DOCUMENTS

| 4,211,333 A | 7/1980 | Villarejos |
| 4,449,640 A | 5/1984 | Finkelstein |

(Continued)

FOREIGN PATENT DOCUMENTS

| WO | WO 2005/004961 A1 | 1/2005 |
| WO | WO 2016/181218 A1 | 11/2016 |

OTHER PUBLICATIONS

International Search Report received for PCT Patent Application No. PCT/US2018/058352, dated Jan. 24, 2019, 2 pages.
(Continued)

*Primary Examiner* — Quynh-Nhu H. Vu
(74) *Attorney, Agent, or Firm* — McDonnell Boehnen Hulbert & Berghoff LLP

(57) ABSTRACT

A device for deterring drug abuse includes a housing configured to contain a drug accessible through an access port. The device includes a physical deterrent configured to move from an unsecured position, wherein the access port of the housing is normally accessible, to a secure position, wherein the access port of the housing is normally inaccessible. The device further includes a locking mechanism that is coupled with the physical deterrent. The locking mechanism has a locked mode, wherein the physical deterrent does not normally move from the secure position to the unsecured position. The locking mechanism is further coupled with a deterrent container having a deterrent substance. The device is configured such that attempts to access the drug when the physical deterrent is in the secure position, and when the locking mechanism is in the locked mode, activate the release of the deterrent substance to the drug.

13 Claims, 11 Drawing Sheets

(51) Int. Cl.
*B65D 51/00* (2006.01)
*A61M 5/50* (2006.01)
*B65D 51/22* (2006.01)

(58) Field of Classification Search
CPC .... A61J 1/1437; A61J 2200/70; A61J 7/0007; A61J 7/0084; A61J 7/0445; B02C 19/08; B02C 25/00
See application file for complete search history.

(56) References Cited

U.S. PATENT DOCUMENTS

| | | | |
|---|---|---|---|
| 4,586,622 A | 5/1986 | Walldorf | |
| 4,598,837 A | 7/1986 | Kreiseder et al. | |
| 4,987,136 A | 1/1991 | Kreek et al. | |
| 5,694,919 A | 12/1997 | Rubsamen et al. | |
| 6,415,202 B1* | 7/2002 | Halfacre | A61J 7/0481 221/102 |
| 8,479,919 B2 | 7/2013 | Kaplan et al. | |
| 9,149,533 B2 | 10/2015 | Guido et al. | |
| 9,302,134 B1 | 4/2016 | Nelson et al. | |
| 9,480,644 B2 | 11/2016 | Crystal et al. | |
| 9,707,226 B2 | 7/2017 | Keegan et al. | |
| 9,757,371 B2 | 9/2017 | Haswani et al. | |
| 9,913,778 B2 | 3/2018 | Dvorak et al. | |
| 2006/0034872 A1 | 2/2006 | Woolf | |
| 2006/0157491 A1* | 7/2006 | Whittle | A61J 7/0481 221/9 |
| 2007/0023444 A1* | 2/2007 | Holloway | A61J 1/03 221/7 |
| 2007/0186923 A1 | 8/2007 | Poutiatine et al. | |
| 2009/0215808 A1 | 8/2009 | Yum et al. | |
| 2010/0249045 A1 | 9/2010 | Babul | |
| 2010/0307208 A1* | 12/2010 | Corbin | B65D 55/145 70/158 |
| 2013/0088328 A1* | 4/2013 | DiMartino | A61J 7/0076 340/5.82 |
| 2015/0038898 A1* | 2/2015 | Palmer | A61J 7/0053 604/60 |
| 2016/0158107 A1* | 6/2016 | Dvorak | A61J 7/0084 241/25 |
| 2017/0231870 A1 | 8/2017 | Stachler et al. | |

OTHER PUBLICATIONS

Written Opinion received for PCT Patent Application No. PCT/US2018/058352, dated Jan. 24, 2019, 8 pages.
Denver7—The Denver Channel, "Safe Rx creates secure medicine bottle to curb teen drug use," YouTube, Retrieved from https://www.youtube.com/watch?v=1WCKgPP2x6U&feature=youtu.be, 2:27, Aug. 22, 2016 (1 page showing URL provided).
E-pill, LLC, "e-pill MedTime SAFE Tamper Resistant Automatic Pill Dispesnser," https://www.epill.com/epillsafe.html, 4 pages, 2017.
GeneSYS-RX, Inc., "Rx MyDOSE," GeneSYS-RX, https://www.genesysrx.com/product/rx-mydose/, 3 pages, 2016.
GeneSYS-RX, Inc., "Our Patented Technology," GeneSYS-RX, https://www.genesysrx.com/our-patented-technology/, 3 pages, 2016.
Margolis, "Exploring Packaging, Storage, and Disposal Solutions to Enhance Opioid Safety," Duke-Margolis Center for Health Policy Conference Center, 9 pages, Jun. 1, 2017.
Tobias, "Warning: Scary Flaws Discovered in Childproof Drug Containers," Forbes, https://www.forbes.com/sites/marcwebertobias/2011/10/31/child-proof-drug-containers-that-dont-work/#67371dac4560, 8 pages, Oct. 31, 2011.

* cited by examiner

DEVICE FOR DETERRING ABUSE OF DRUGS

CROSS-REFERENCE TO RELATED APPLICATIONS

This patent application is a continuation-in-part application of, and therefore claims priority from, U.S. patent application Ser. No. 15/800,469, entitled "Device for Deterring Abuse of Drugs," filed on Nov. 1, 2017 and is hereby incorporated herein by reference in its entirety.

FIELD OF THE INVENTION

The invention generally relates to devices and methods for deterring drug abuse, more particularly, the invention relates to a locking mechanism that dispenses a deterrent when the drug is improperly accessed.

BACKGROUND OF THE INVENTION

The opioid crisis has greatly increased the risk of medication diversion, i.e., when a legal controlled substance is used illegally. The drug theft occurs frequently in outpatient facilities, but can happen anywhere. The theft can come from a number of sources including the patient, friends and family of the patient, and even health care workers struggling with addition. Stealing medication from an IV line or a syringe and replacing it with another substance to prevent detection can lead to dangerous bloodstream infections.

SUMMARY OF VARIOUS EMBODIMENTS

In accordance with one embodiment of the invention, a device for deterring drug abuse includes a housing configured to contain a drug that can be accessed through an access port of the housing. The device also includes a physical deterrent configured to move from an unsecured position, wherein the access port of the housing is normally accessible, to a secure position, wherein the access port of the housing is normally inaccessible. The device further includes a locking mechanism that is coupled with the physical deterrent. The locking mechanism has a locked mode, wherein the physical deterrent is not normally able to move from the secure position to the unsecured position. The locking mechanism is further coupled with a deterrent container that has a deterrent substance therein. The device is configured such that attempts to access the drug through the access port: a) when the physical deterrent is in the secure position, and b) when the locking mechanism is in the locked mode, activate the release of the deterrent substance to the drug.

The drug may be accessed by moving the physical deterrent relative to the housing. To that end, the physical deterrent may be oriented relative to the housing in such a way as to prevent and/or significantly hinder access to the access port when in the locked mode, and the physical deterrent may be oriented relative to the housing in such a way to allow access to the access port when in the unlocked mode.

In some embodiments, the locking mechanism may have an unlocked mode where the physical deterrent is normally able to move from the secured position to the unsecured position.

Among other things, the physical deterrent may be a lid of a container. Alternatively, the physical deterrent may be a cap, or a box. The deterrent device may be internal, external, and/or built-in to the housing.

In some embodiments, a plug may keep the deterrent substance in the deterrent container. Among other ways, pressurized gas from walls of the housing may support the plug. Additionally, or alternatively, a spring may support the plug. Alternatively, or additionally, the housing may contain wires that detect attempts to access the drug.

Illustrative embodiments may include a touchscreen interface. The touchscreen may provide reminders regarding a drug dosing schedule. The touchscreen interface may be configured to receive a passcode. If a correct passcode is entered, the drug may be dispensed, for example, through a chute. A carousel may dispense the drug through the chute. Furthermore, a sensor may detect tampering with the chute, and may open a valve that reduces the pressure in the walls of the housing. Accordingly, the plug will no longer block the deterrent container, and the deterrent is released. A process may control the valve to open after a specified time interval, such as one-month, three-months, six-months, or after an expiration date of the drug. Additionally, or alternatively, a signal may be sent, for example from a medical provider through Wi-Fi, to open the valve.

In accordance with another embodiment of the invention, a device for deterring drug abuse includes a housing configured to contain a drug that can be accessed through an access port of the housing. The device also includes a physical deterrent configured to move from an unsecured position, wherein the access port of the housing is normally accessible, to a secure position, wherein the access port of the housing is normally inaccessible. The device further includes a locking mechanism that is coupled with the physical deterrent. The locking mechanism has a locked mode, wherein the physical deterrent is not normally able to move from the secure position to the unsecured position. The locking mechanism also has an unlocked mode, wherein the physical deterrent is normally able to move from the secured position to the unsecured position. The locking mechanism is further coupled with a deterrent container that has a deterrent substance therein. Moving the physical deterrent relative to the housing when the locking mechanism is in the locked mode activates the release of the deterrent substance to the drug.

The physical deterrent may be oriented relative to the housing in such a way as to prevent or significantly hinder access to the access port when in the locked mode. The physical deterrent may be internal and/or external to the housing. Furthermore, the physical deterrent may be oriented relative to the housing in such a way to allow access to the access port when in the unlocked mode. The housing and the physical deterrent may be movable with respect to one another.

For example, a rod that is connected to the housing and the physical deterrent may be used to change the orientation of the housing relative to the physical deterrent. The rod is normally movable in the unlocked mode and normally immobile in the locked mode. The housing may be rotatable relative to the physical deterrent in the unlocked mode. Additionally, the housing may be not rotatable relative to the physical deterrent in the locked mode.

Among other things, the housing may include an IV fluid bag, a vial, a bottle, a canister, and/or a syringe. Cutting a wall of the housing may release the deterrent substance. To that end, the housing may have hollow walls filled with pressurized gas (e.g., pressurized air and/or compressed nitrogen). When the walls are cut (e.g., by someone trying to improperly access the drug by cutting through the wall), the pressure drop activates the release of the deterrent substance. Additionally, or alternatively, the housing wall may be covered in a matrix of electrically conductive material, e.g., wire. When the electrically conductive material is cut (e.g., by someone trying to improperly access the drug by cutting through the wall), the release of the deterrent substance is activated.

Among other choices, the deterrent substance may be one or more of a drug antagonist (e.g., naloxone, naltrexone, etc.), a colorant (e.g., bright colorant), an emetic (e.g., ipecac syrup), a foul odor (e.g., pepsin, butanethiol, etc.), a gelling agent, an encapsulating agent (e.g., glue), a flushing agent (e.g., niacin), and/or an irritant (e.g., capsaicin). Among other things, the locking mechanism may include a padlock, combination lock, and/or a biometric scanner. The locking mechanism may also be coupled to a dosage counter that calculates the amount of drug released. The locking mechanism may lock after a certain dosage has been released from the housing. Additionally, or alternatively, the locking mechanism may be coupled to a timer that locks the locking mechanism after a predefined time.

In accordance with an embodiment of the invention, a device for deterring drug abuse includes a housing containing therein a drug. The device also includes a locking mechanism coupled with the housing. The locking mechanism has a locked mode wherein the drug is normally inaccessible, and an unlocked mode wherein the drug is normally accessible. The locking mechanism is further coupled with a deterrent container having a deterrent substance therein. Attempts to access the drug when the physical deterrent is in the secure position and the locking mechanism is in the locked mode activate the release of the deterrent substance.

In accordance with another embodiment of the invention, a method of accessing a drug includes providing a housing configured to contain a drug. The housing has an access port through which the drug can be accessed. A movable physical deterrent blocks the access port of the housing when the physical deterrent is in a secure position. A locking mechanism prevents and/or significantly hinders the physical deterrent from moving from the secure position to an unsecured position wherein the physical deterrent no longer blocks the access port. A deterrent container is configured to hold a deterrent substance therein that releases when the drug is accessed while the physical deterrent is in the secure position and the locking mechanism is in the locked mode. The method next unlocks the locking mechanism. The physical deterrent is moved into the unsecure position, and the drug is accessed.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments a device provides secure access to a drug and deters unauthorized access of the drug. The device includes a locking mechanism coupled to a physical barrier that prevents and/or mitigates access to the drug by unauthorized users, unauthorized dosages, and/or at unauthorized times. If the housing is improperly breached, a chemical deterrent is released. The chemical deterrent mixes with the drug, making the drug unsuitable for use.

Figure 1:
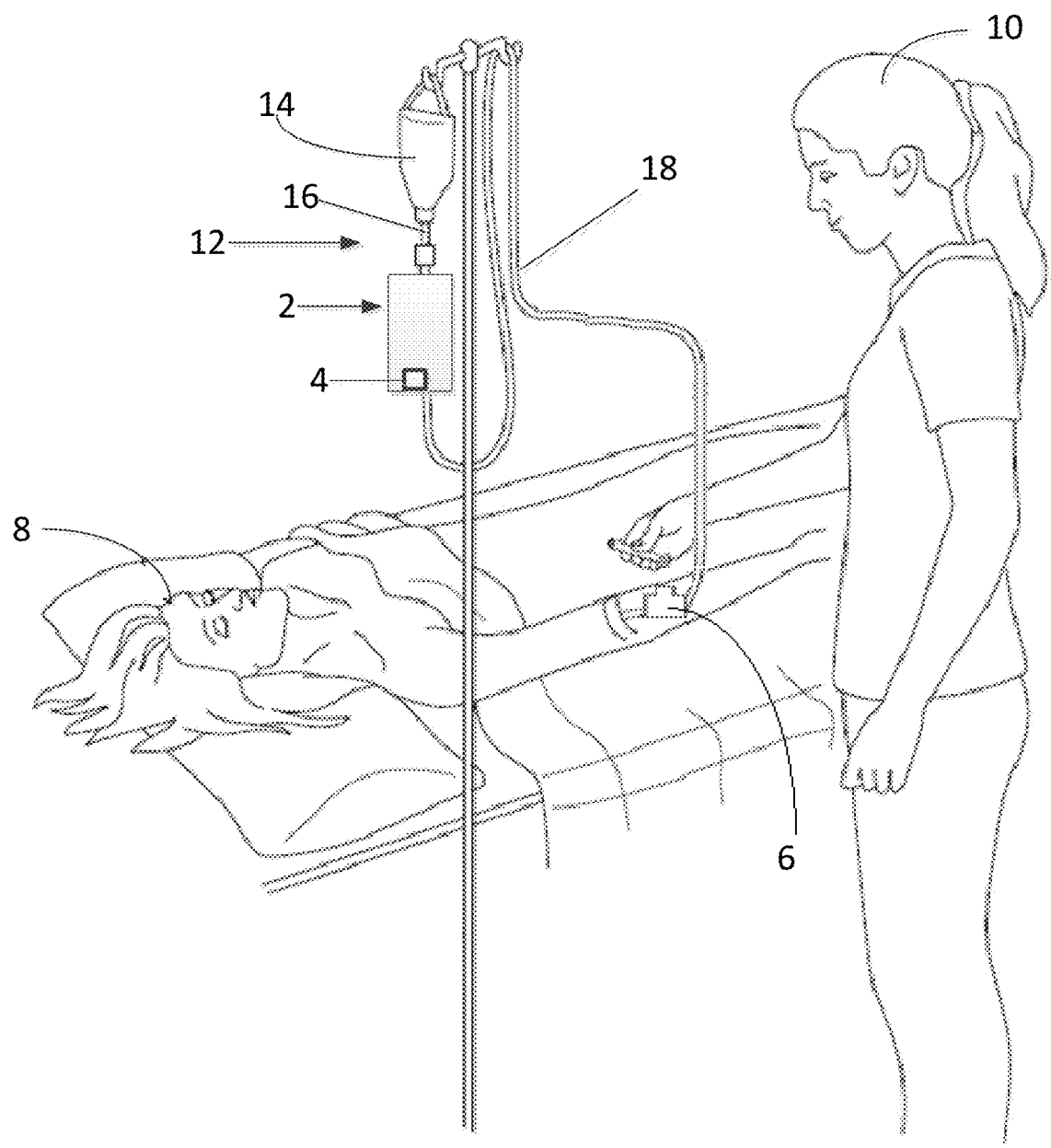
FIG. 1 schematically shows a use of a device for deterring drug abuse configured in accordance with illustrative embodiments of the present invention.

FIG. 1 schematically shows a use of a device 2 for deterring drug 4 abuse configured in accordance with illustrative embodiments of the present invention. The device 2 may serve as the primary packaging of the drug 4, e.g., drug 4 that needs to be reconstituted prior to intravenous infusion. A catheter 6 may connect with a patient's vein (the patient is identified by reference number 8). Adhesive tape or similar material may be coupled with the catheter 6 and the patient's 8 arm to ensure that the needle remains in place. It should be understood that illustrative embodiments are not limited to drugs 4 that require reconstitution, and such drugs 4 are merely presented as examples.

Prior art drug delivery and administration methods generally require multiple steps and multiple intermediate parties to deliver the drug 4 from manufacture to patient 8. For example, a pharmacist at the hospital may need to compound the drug 4, a health care worker may transfer the drug 4, and a nurse 10 may deliver the drug 4. Other situations where this may arise include, for example, in a hospital, nursing home, palliative care, or substance abuse treatment center settings. It is also possible that a patient 8 may seek to abuse illicit or prescription drugs 4 and inject them into their own intravenous (IV) set 12. It is also possible to steal and abuse prescription IV drug sets 12.

Thus, the prior art methods have high potential for drug 4 diversion and/or abuse. Furthermore, in some cases, the drug 4 may be left unattended/unmonitored for periods of time (e.g., in an IV bag 14 connected to a sleeping patient 8). Thus, the patient 8, health care workers, patient's friends and family as well as others have the ability to illegally remove/ take some, or the entirety, of the legally prescribed drug 4. Illustrative embodiments deter the abuse of drugs 4.

Illustrative embodiments of the invention may be integrated into the IV set 12 by providing a physical deterrent and a chemical deterrent. Thus deterring the use of the IV set 12 for abuse of illicit or prescription drugs 4. Illustrative embodiments may be useful, for example, when the IV set 12 is used to administer prescription pain killers 4. Drugs 4 such as morphine sulphate, hydromorphone, fentanyl, and methadone are particularly susceptible to abuse. When contained in a prescription IV set 12, the set deters the removal, contamination, insertion, over-administration, or abuse of the drug 4. Illustrative embodiments also deter the insertion of drugs 4 of abuse into an IV set 12.

Figure 2:
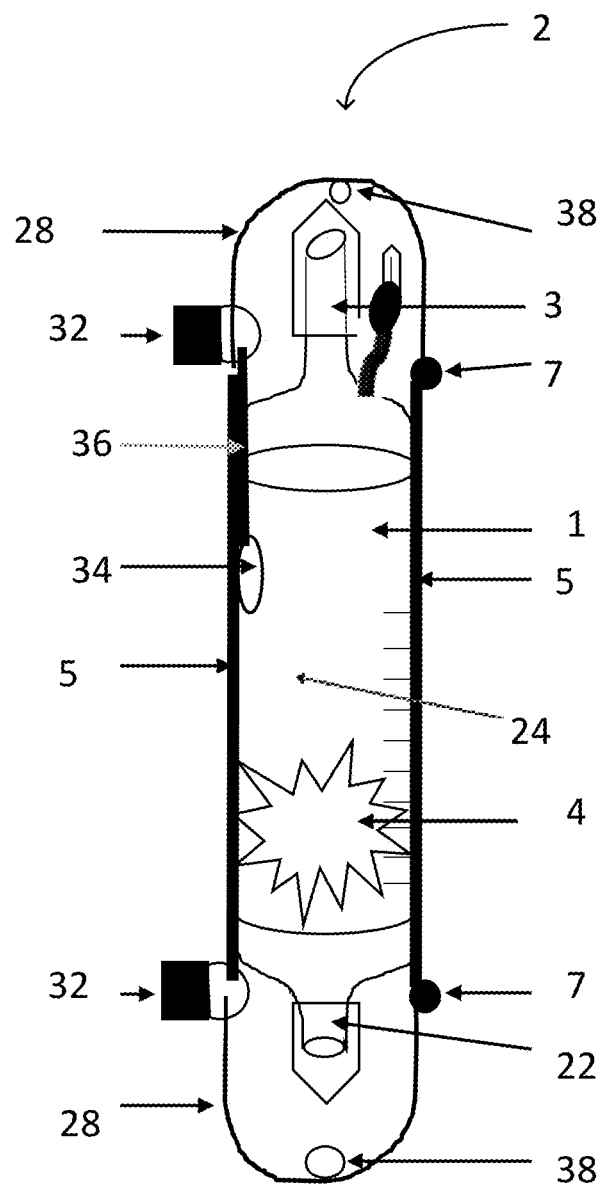
FIG. 2 schematically shows a device for deterring drug abuse in a secured position in accordance with illustrative embodiments of the present invention.

FIG. 2 schematically shows a device 2 for deterring drug 4 abuse in accordance with illustrative embodiments of the present invention. The device 2 prevents and/or mitigates abuse of a drug 4 that is to be administered to the patient 8 (e.g., a patient 8 having a disease or managing pain). In illustrative embodiments, the device 2 is integrated with a drug housing 1. The drug 4 in the housing 1 may be dry or reconstituted.

In illustrative embodiments, the housing 1 is a cylinder 24 (e.g., a transparent cylinder 24 with volume graduation markings). In some embodiments, the transparent cylinder 24 has a first end that has a first spike 3 that is configured to pierce the port of an IV bag 14. The first spike 3 is configured to pierce the IV fluid bag 14 and to form a fluid connection between the cylinder 24 and the IV fluid bag 14. The transparent cylinder 24 also has a port 22 that is configured to be pierced by a spike of an IV tubing 18 (shown in FIG. 1) so as to form a fluid connection between the cylinder 24 and the tubing 18 that connects to the patient 8.

Although the terms "spike" and "port" are used to distinguish different access points of the drug 4, both of these terms are considered to be "access ports" of the housing, i.e., the drug 4 may be accessed through these fluid passageways. Furthermore, although illustrative embodiments are described as having a "spike" and "port" it should be understood that these are merely exemplary and that illustrative embodiments are not limited to having a spike and/or a port. For example, although some embodiments are described as having the spike 3, other embodiments may not have the spike 3. Instead, for example, intermediary tubing 18 may connect the access port (shown as spike 3) to another spike outside of the device 2 that then connects to the IV bag 14.

In some embodiments, walls 5 of the device 2 are formed from an impervious material, such as polycarbonate, polypropylene, polyethylene, terephthalate, high density polyethylene, polyvinyl chloride, polystyrene, polylactide, and/or glass (e.g., chemically strengthened glass). The walls 5 (and the device 2) may be integrally formed with the cylinder 24, or the cylinder 24 may be positioned within the walls of an independent device 2. The walls 5 are of a sufficient thickness and rigidity to prevent and/or significantly mitigate squeezing of the cylinder 24 (e.g., as by a human grip trying to deform and/or open the cylinder 42). The walls 5 also prevent and/or significantly mitigate unauthorized penetration by needles.

On both ends of the cylinder 24 are physical deterrents. The physical deterrents may be, for example, caps 28 that are attached to the wall 5 by a secure hinge 7. In illustrative embodiments, the caps 28 may be formed from polycarbonate, polypropylene, polyethylene terephthalate, high density polyethylene, polyvinyl chloride, polystyrene, polylactide, glass (e.g., chemically strengthened glass), and/or another clear material that is sufficiently thick and rigid to prevent and/or significantly hinder needle penetration and/or easy breaking of the caps 28.

When the physical deterrent is positioned in such a way as to significantly hinder and/or prevent physical access to the drug 4, the physical deterrent 20 is in a secure position. FIG. 2 schematically shows the physical deterrent 20 (i.e., caps 28) in the secure position. In contrast, when the physical deterrent 20 does not mitigate and/or prevent physical access to the drug 4, the physical deterrent 20 is in an unsecured position. Thus, when the locking mechanism 32 is unlocked and the cap 28 is opened (e.g., rotated around the secure hinge 7), users may access the drug 4 inside the container, and the physical deterrent is in the "unsecured position." The physical deterrent can be in the unsecured position and still be in a locked mode. The locked mode prevents and/or significantly mitigates the movement of the physical deterrent 20 from the secured position to the unsecured position and vice-versa.

The caps 28 are lockable either by multiple locking mechanisms 32 on the top and bottom, or by a single locking mechanism 32 that locks both the top and bottom. The lock 32 may be an external lock (e.g., a padlock) or integrated into the device 2 (e.g., biometric scanner). The lock 32 may be opened by a key, keypad, combination lock, or other suitable mechanism.

The hinge 7 and/or lock 32 attachment may be anchored 36 to a compartment 34 (also referred to as a "deterrent container 34") that houses a deterrent. The deterrent may be a drug antagonist, such as naloxone, a gelling agent, and/or other deterrent substance such as capsicum. The anchor 36 is attached to the cylinder 24 wall by glue, lamination, and/or some other semi-permanent or permanent means. If one or more of the caps 28 is forced open, the anchor 36 breaks away from the cylinder 24 and tears open the deterrent container 34 and releases the deterrent into the main compartment of the cylinder 24 where it contacts the drug 4. Accordingly, the drug 4 in the cylinder 24 is rendered unsuitable for use and abuse of the drug 4 is deterred. Illustrative embodiments do not necessarily require the anchor 36 and/or the compartment 34.

When the physical deterrent 20 is in the secured position (e.g., cap 6 is closed), and the locking mechanism is in the locked mode (e.g., padlock 32 is locked and keeps the caps 6 in their position), as shown in the figure, the drug 4 is normally inaccessible. This means that a user is not able to open the container and access the drug 4. The term "normally" is used to refer to situations where a user may try to open the device 2 with his or her hands, and includes the forces that the device may encounter in its ordinary use. "Normally" distinguishes other situations where power tools and/or other tools and methods may be used to break apart the physical deterrent and/or the locking mechanism 32. Accordingly, if the physical deterrent is opened when the device 2 is in the closed mode and the locking mechanism is locked (e.g., by an unauthorized user), the deterrent is released. Conversely, if the physical deterrent 20 is opened when the device 2 is in the opened mode and the locking mechanism is unlocked (e.g., by an authorized user), the deterrent is not released.

The physical deterrent 20 may have a small slit or hole 38 to allow IV tubing 16, 18 to remain connected to the device 2 while the physical deterrent 20 is in the secured position. Even in such a configuration, the access port of the housing 1 is considered to be "normally inaccessible." Although illustrative embodiments are shown as blocking access to the outside of the access port, it should be understood that some embodiments may have the physical deterrent 20 internal to the housing 1 and block the access port internally.

Figure 3:
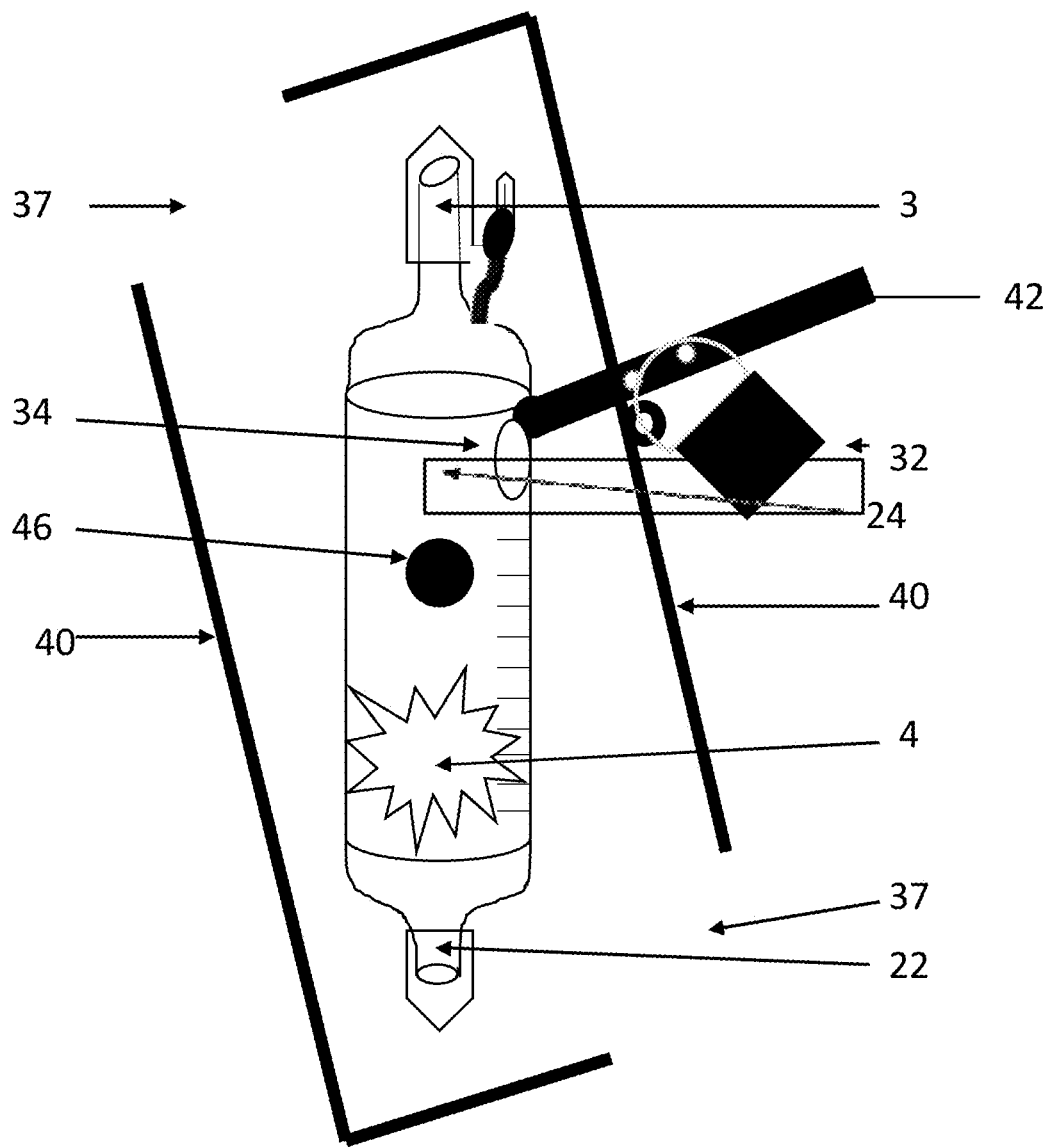
FIG. 3 schematically shows an alternative embodiment of the device in a secured position in accordance with illustrative embodiments of the invention.
Figure 4:
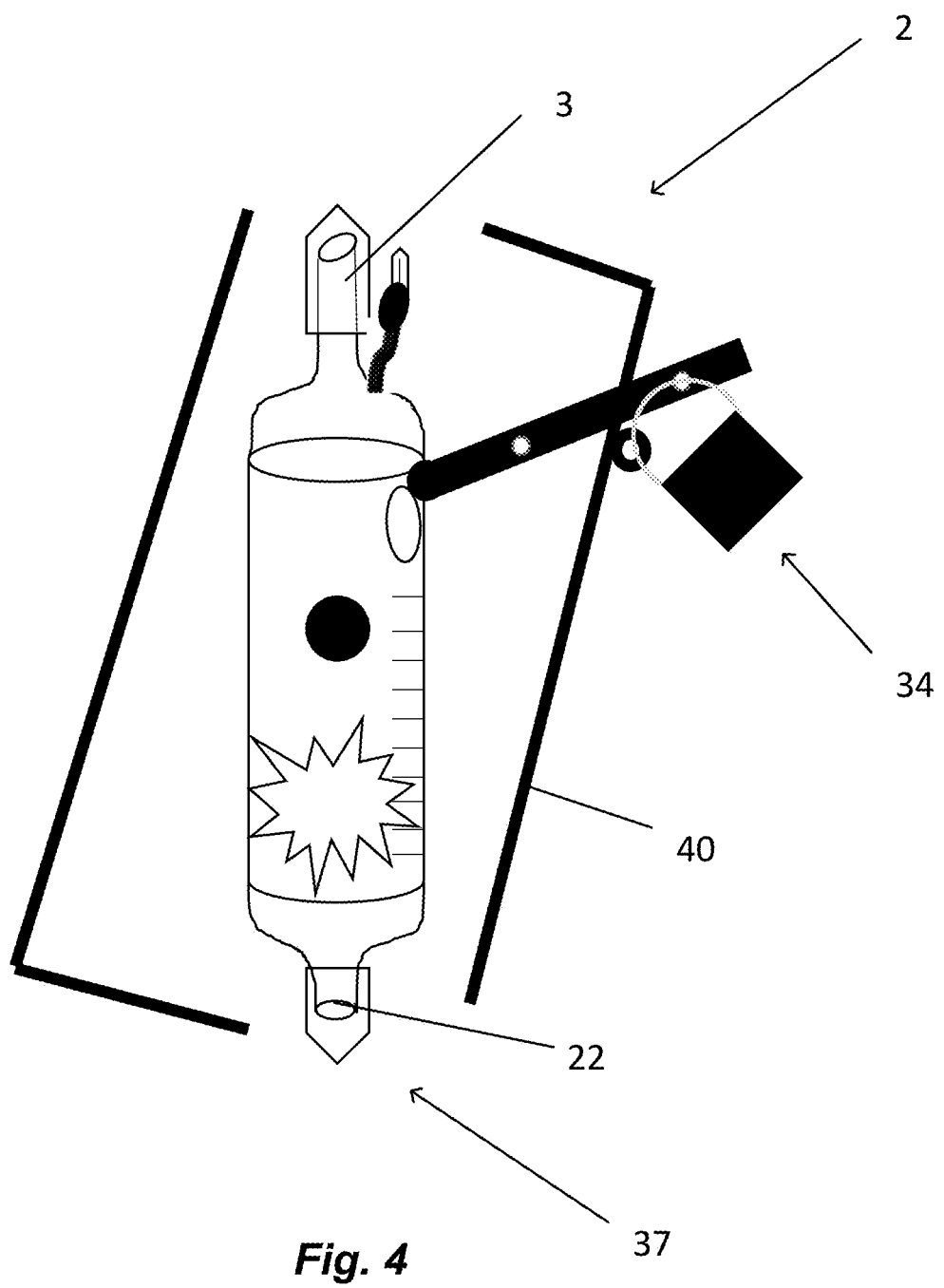
FIG. 4 schematically shows the device of FIG. 3 in an unsecured position in accordance with illustrative embodiments of the invention.

FIGS. 3-4 schematically show an alternative embodiment of the device 2 for deterring drug abuse in accordance with illustrative embodiments of the present invention. As described above, the housing 1 (e.g., transparent cylinder 24) has the drug 4 therein. The cylinder 24 has a first end that has a first spike 3, and a second end that has a port 22. The first spike 3 is configured to pierce an IV fluid bag 14 and to form a fluid connection between the cylinder 24 and the IV fluid bag 14 (shown in FIG. 1). The port is configured to be pierced by a second spike that is part of a tubing 18 (shown in FIG. 1), thereby forming a fluid connection between the cylinder 24 and the tubing 18. At least a portion of the volume of the cylinder 24 is occupied by the drug 4.

The cylinder 24 is securely integrated inside a physical deterrent 20 (e.g., rectangular box 40, shown as a partial rectangle), which may be formed from an impervious material, such as polycarbonate, polypropylene, polyethylene terephthalate, high density polyethylene, polyvinyl chloride, polystyrene, polylactide, glass (e.g., chemically strengthened glass). The walls 5 of the physical deterrent 20 are of a sufficient thickness and rigidity to prevent and/or significantly hinder squeezing of the cylinder 24. The walls 5 also prevent and/or mitigate unauthorized penetration by needles. This is a mechanism to prevent and/or significantly hinder and/or deter abuse of the drug 4 contained within.

In some embodiments, the housing 1 is connected with the physical deterrent (e.g., barrier 40) at a pivot point 46 that allows the housing 1 to rotate partially or entirely within the barrier 40. For example, the middle of the housing 1 is connected to the middle of the barrier 40 by the pivot point 46 that allows the housing 1 to rotate partially within the barrier 40. There is an opening 7 on opposite ends of the top and bottom of the barrier 40.

FIG. 3 schematically shows the device 2 in a secured position in accordance with illustrative embodiments of the invention. FIG. 4 schematically shows the device 2 of FIG. 3 in an unsecured position in accordance with illustrative embodiments of the invention. If the cylinder 24 is pivoted one way, both ends 3 and 22 are accessible through the openings 37 in the barrier (shown in FIG. 4). When the cylinder 24 is pivoted another way, both ends 3 and 22 are inaccessible because they are shielded by the solid portion of the barrier 40 (shown in FIG. 3).

There may be a small slit (not shown) cut into the solid portion of the barrier 40 to allow tubing to be connected to the cylinder 24 while it is in the inaccessible position shown in FIG. 3. The tubing may be connected through the slit, for example, when the device 2 is in the accessibly position shown in FIG. 4. A rod 42 connects the cylinder 24 and the barrier. In some embodiments, the rod 42 extends through the barrier 40. Pulling the rod 42 changes the angle of the cylinder 24 relative to the barrier 40 and causes the device to move 2 from the secured position to the unsecured position and vice-versa. The position of the rod 42 is lockable either by an external lock 32, such as a padlock, or a locking mechanism 32 integrated into the rod 42 and/or the barrier 40. The rod 42 may be anchored to a deterrent container 34 that houses an antagonist, such as naloxone or naltrexone, a gelling agent and/or other deterrent substance such as capsicum. When the cylinder 24 is forced away from the rod 42, the container 34 ruptures and releases the deterrent into the cylinder 24. Thus, the contents of the cylinder 24 are rendered unfit for use, and thereby deter abuse.

Illustrative embodiments may contain naltrexone as, or part of, the deterrent substance. Naltrexone (e.g., naltrexone hydrochloride) is an opioid antagonist. Naltrexone markedly attenuates or completely blocks, reversibly, the subjective effects of intravenously administered opioids. Illustrative embodiments may administer a drug antagonist (such as, for example, Naltrexone) that is not associated with the development of tolerance or dependence. Clinical studies indicate that 50 mg of naltrexone hydrochloride may block the pharmacologic effects of 25 mg of intravenously administered heroin for periods as long as 24 hours. Other data suggest that doubling the dose of naltrexone hydrochloride provides blockade for 48 hours, and tripling the dose of naltrexone hydrochloride provides blockade for about 72 hours. There is limited clinical experience with naltrexone over dosage in humans. In one study, subjects who received 800 mg daily naltrexone hydrochloride for up to one week showed no evidence of toxicity.

In the mouse, rat and guinea pig, the oral LD50s were 1,100 to 1,550 mg/kg; 1,450 mg/kg; and 1,490 mg/kg; respectively. High doses of naltrexone hydrochloride (generally ≥1,000 mg/kg) produced salivation, depression/reduced activity, tremors, and convulsions. Mortalities in animals due to high-dose naltrexone administration usually were due to tonic-clonic convulsions and/or respiratory failure. Illustrative embodiments of the device 2 may contain between about 10 mg and about 1200 mg of Naltrexone as the chemical deterrent. Some other embodiments may contain a fixed dose of antagonist per unit dose of drug 4 (e.g., opioid). Other embodiments may contain a fixed dose of antagonist per unit dose of drug 4 (e.g., opioid). As an example, between 2.5 mg and 30 mg of antagonist may be used per drug dose. Furthermore, illustrative embodiments contain a dosage of chemical deterrent that preferably does not cause over dosage in humans.

Figure 5:
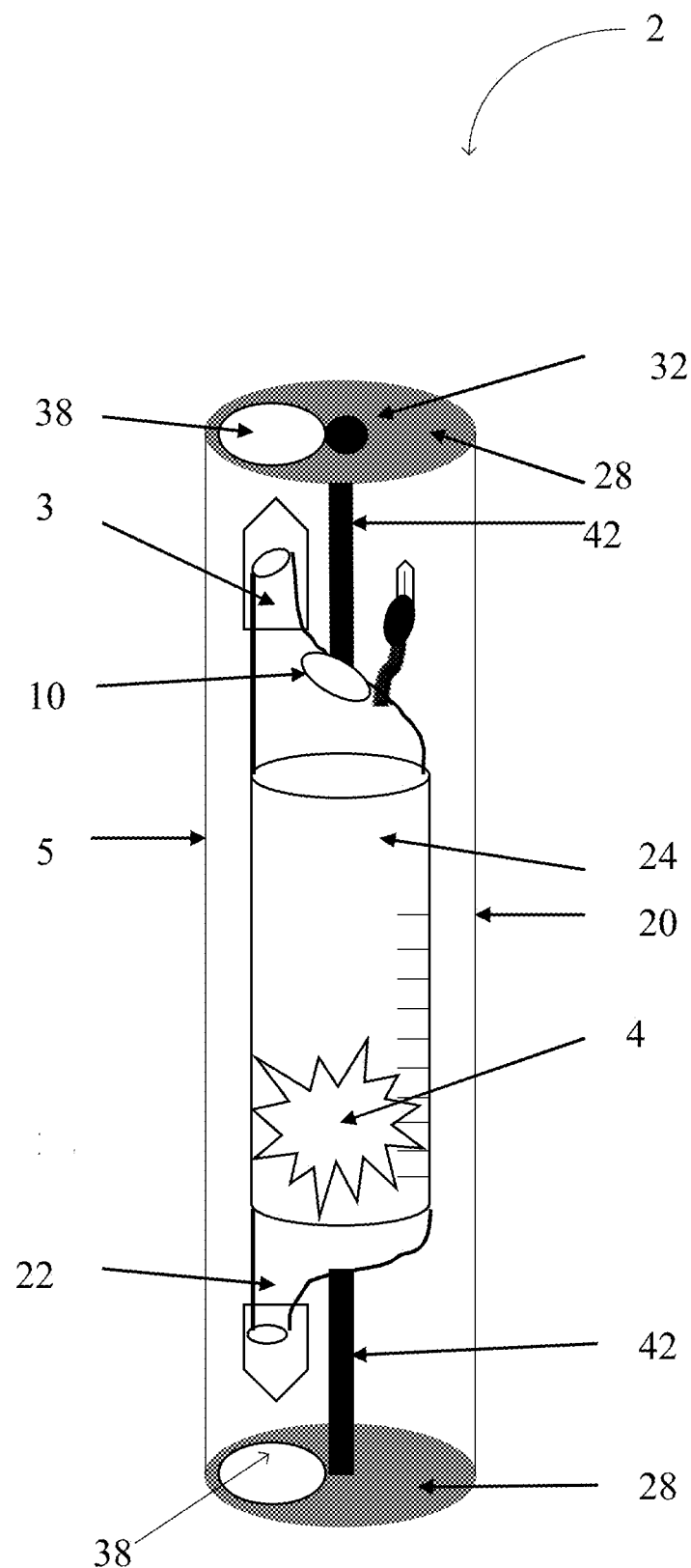
FIG. 5 schematically shows another alternative embodiment of the device in an unsecured position in accordance with illustrative embodiments of the invention.

FIG. 5 schematically shows another alternative embodiment of the device 2 in accordance with illustrative embodiments of the invention. The device 2 houses a drug 4 that is to be administered to a patient 8 that has a disease. To that end, the device has a housing 1 (e.g., transparent cylinder 24) that is configured to house the drug 4. The cylinder 24 has a first end that has a first spike 3 which is offset from the central axis of the cylinder, and the first end is opposite a second end that has a port 22 which is offset from the central axis of the cylinder. The first spike 3 is configured to pierce an IV fluid bag (not shown) and to form a fluid connection between the cylinder 24 and the IV fluid bag. The port 22 is configured to be pierced by a second spike that is part of a tubing (not shown), thereby forming a fluid connection between the cylinder and the tubing. At least a portion of the volume of the cylinder 24 is occupied by the drug 4.

The housing 1 is enclosed in the physical deterrent 20 (e.g., larger cylinder 20) formed from an impervious material such as polycarbonate, polypropylene, polyethylene terephthalate, high density polyethylene, polyvinyl chloride, polystyrene, polylactide, and/or glass (e.g., chemically strengthened glass). The walls are of a sufficient thickness and rigidity to prevent and/or significantly hinder squeezing of the cylinder 24. The walls also prevent and/or significantly hinder unauthorized penetration by needles. This is a mechanism to prevent and/or significantly hinder and or deter abuse of the device or drug contained within. The impervious cylinder has caps 28 on both ends. The caps have a hole 38 toward the side of the top or bottom. A central rod 42 runs from the middle of the upper cap 28 to the middle of the lower cap 28. The inner cylinder 24 can rotate on the rod 42. When the reconstitution cylinder 24 rotates within the impervious cylinder 20 in one position (i.e., the unsecured position) the access ports 3 and 22 line up with the holes 38 and are accessible (as shown in FIG. 5).

In another position (i.e., the secured position—not shown) the access ports 3 and 22 are shielded and are inaccessible. A locking mechanism 32 can lock the position of the inner cylinder 24 either in the unsecure or secure position. If the holes 38 on the impervious cylinder 5 are on diagonal ends, it would allow for operations such as filling the reconstitution cylinder 24 through spike 3 while preventing and/or significantly hindering access to the access port 22. Then the access port 22 could be rotated to be accessible while preventing and/or significantly hindering access to the top spike 3. Additionally, or alternatively, if the inner cylinder 24 is manufactured with a constituted drug 4 inside, there may be no need to have a hole 38 for filling the reconstitution cylinder 24. The rod 42 may be anchored to a container 10 that houses an antagonist, such as naloxone, a gelling agent, and/or other deterrent substance, such as capsicum. If the cylinder 24 is forced to open in the secured position, then the container 34 ruptures and releases the deterrent into the cylinder 24. Thus, the contents are rendered unfit for use, and thereby deter abuse.

Preferably, the device 2 may be provided in a sterile packaging and may have a premeasured amount of the drug 4 in the cylinder 24. Moreover, the device may be provided in tamper-evident packaging.

Furthermore, the cylinder 24 may be fluidly connected with the IV fluid bag 14. This connection facilitates the reconstitution of the drug 4. Alternatively, or additionally, the cylinder 24 may come prepackaged with a constituted drug 4. In this case the cylinder 24 does not need to be configured to connect to an IV bag 14. The tubing 18 additionally may be connected to the patient 8. To facilitate delivery of the drug 4 to the patient 8, the cylinder 24 may be fluidly connected with the tubing 18 connected to the patient 8.

Figure 6:
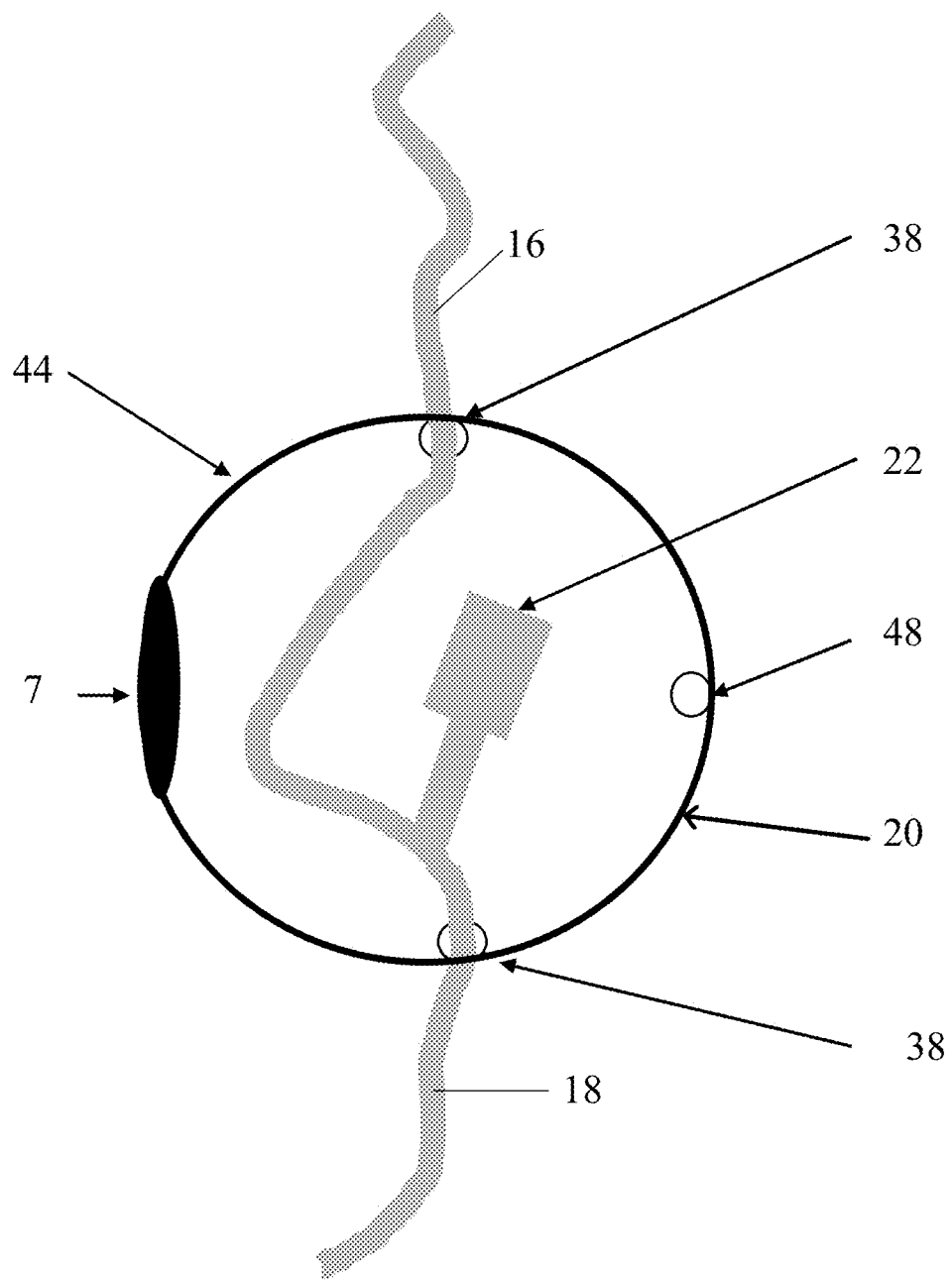
FIG. 6 schematically shows another alternative embodiment of the device in accordance with illustrative embodiments of the invention.

FIG. 6 schematically shows another alternative embodiment of the physical deterrent 20 in accordance with illustrative embodiments of the invention. To prevent and/or significantly hinder unauthorized injection of drugs 4 into open ports 22 and junctions of the IV tubing, the ports 22 and or junctions are enclosed in an abuse deterrent device 20 (e.g., shell 44). An example of a port is an access port 22 for push medications. Another example would be a needleless port for a piggyback IV. The shell 44 (also referred to as sphere 44) is formed from a hard clear material such as polycarbonate, polypropylene, polyethylene terephthalate, high density polyethylene, polyvinyl chloride, polystyrene, polylactide, and/or glass (e.g., chemically strengthened glass). The shell 44 is sufficiently hard and thick to prevent and/or significantly hinder unauthorized injections into the port 22. This is a physical mode of abuse deterrence.

The shell 44 can be a hollow sphere. The sphere 44 may be made in two parts that are connected by a hinge 7. A locking mechanism 32, such as a padlock, may be inserted through two holes 48 on the sphere 44 and then locked. The locking mechanism 32 can also be integrated into the sphere 44 (e.g., biometric scanner). In some embodiments, the sphere 44 also has at least two holes 38 to allow IV tubing to be connected while in the secured position. One hole 38 is for the IV line 16 to enter from the IV bag 14 or reconstitution cylinder. The other hole 38 is for the tubing 18 to exit to the patient 8.

Figure 7:
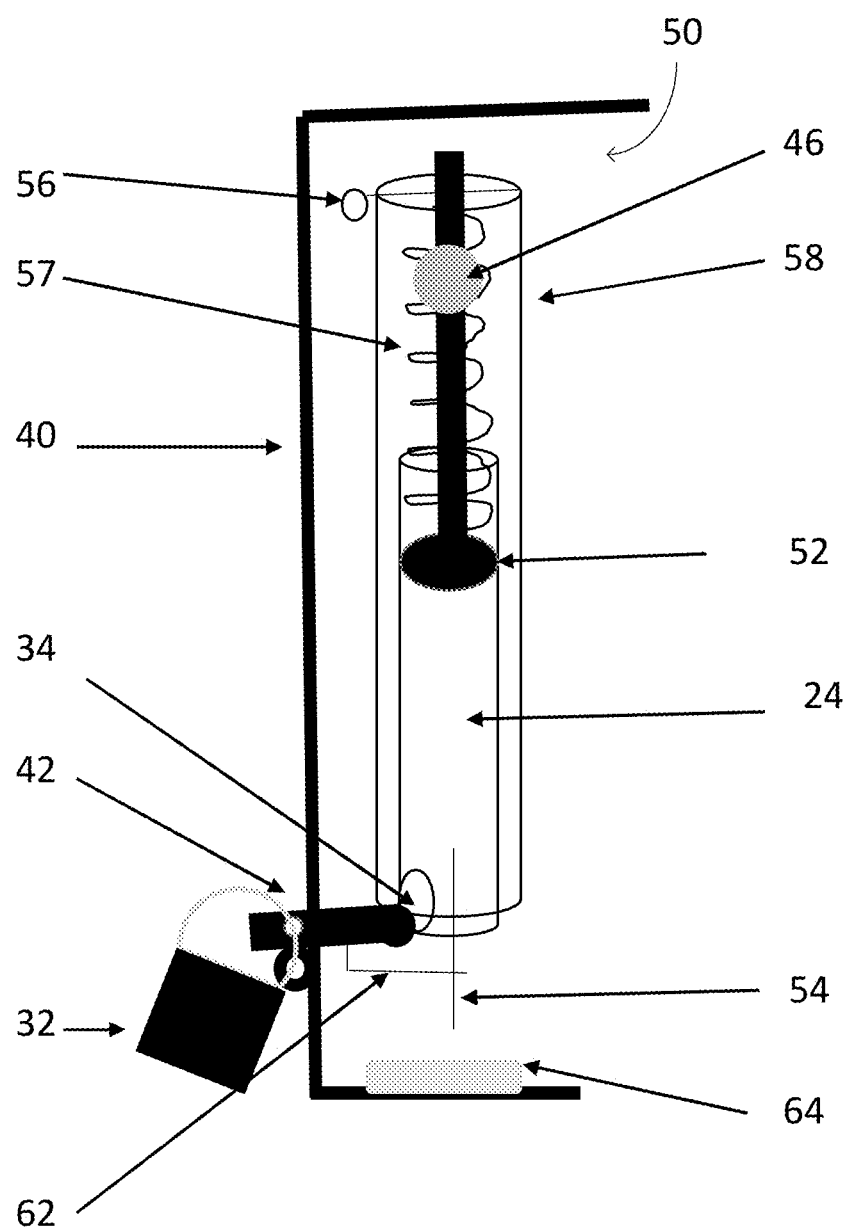
FIG. 7 schematically shows another alternative embodiment of the device in the secured position in accordance with illustrative embodiments of the invention.

FIG. 7 schematically shows another alternative embodiment of the physical deterrent 20 in the secured position in accordance with illustrative embodiments of the invention.

Illustrative embodiments provide an abuse deterrent prefilled automatically injecting syringe 50. A housing 1 (e.g., cylinder 24) holds a liquid medicine suitable for injection. The cylinder 24 is prefilled at the manufacturer with the medicine. The cylinder 24 is configured as a syringe 50. The cylinder 24 can be formed from glass or plastic, or any other material that is suitable for direct contact with an injectable medicine.

Illustrative embodiments include a plunger 52 that pushes the drug 4 through the needle 54. A firing pin 56 holds the plunger 52 in place. The firing pin 56 is secured to an outer cylinder 58, and the outer cylinder 58 is secured to the inner cylinder 24. The outer cylinder 58 can also be distally anchored to the rod 42 and or deterrent container 34. Removing the firing pin 56 allows the spring 57 to push the plunger 52 and inject the medicine in the cylinder 24 into the patient through the needle 54.

The syringe is held inside a physical deterrent 20, such as rectangular box 40. The rectangular box 40 may me formed from a rigid material, such as a hard plastic. Additionally, the box 40 may be formed from clear plastic such as polycarbonate, polypropylene, polyethylene terephthalate, high density polyethylene, polyvinyl chloride, polystyrene, and/or polylactide. One side of the box 40 is open. The syringe 50 is secured in the box 40 on one side by a pivot 46. The pivot 46 allows the syringe 50 to rotate out of the box 40 so that the needle 54 may insert into a patient 8 for the purpose of administering a medicine. On the other side, the syringe 50 is held by a rod 42 that is secured to the box 40 by a lock 32.

The rod 42 is anchored to the deterrent container 34 having a deterrent substance. Although the deterrent container 34 is shown as taking up only part of the bottom of the cylinder 24, it should be understood that the container 34 can be modified to fill more or less of the volume of the cylinder 24 and to adjust the amount of medicine that is left after use. If the syringe 50 is forced into the unsecured position (not shown), the deterrent container 34 ruptures and releases the abuse deterrent substance into the cylinder 24 to render the drug 4 unfit for abuse. The deterrent container 34 can be, for example, ripped open when it is pulled away from the rod 42.

As an example, if the cylinder 24 was filled with an opioid 4, the deterrent container 34 may be filled with an opioid antagonist, such as naloxone, naltrexone, and/or a gelling agent. In illustrative embodiments, the rod 42 may have an additional arm 62 that extends around the needle 54. If the syringe is forced open, the arm 62 bends the needle 54 so it cannot be used.

Illustrative embodiments include a sponge 64 that is coated or otherwise impregnated with the chemical deterrent. The sponge 64 may be opposite the needle 54. If the firing pin 56 is activated in the secured position (as shown in FIG. 7), the drug 4 sprays into the sponge 64 containing the antagonist (e.g., which may be dried onto the sponge), which mixes the drug 4 and antagonist and renders the drug 4 unsuitable for use. The box 40 can be packaged inside an outer box (not shown) that is secured in place by the rod 42. The outer box may provide an added layer of protection from tampering.

Illustrative embodiments do not require a spring 57, firing pin 56 and/or the outer cylinder 58 to cover more than half the length of the inner cylinder 24. The outer cylinder 58 may slide freely on the inner cylinder 24. The syringe 50 may be manually injectable. When the syringe 50 is unlocked, it may be injected by pressing the needle 54 into the patient 8 and pushing the syringe 50 down to collapse the outer cylinder 58 and inner cylinder 24 to administer the medicine.

Figure 8:
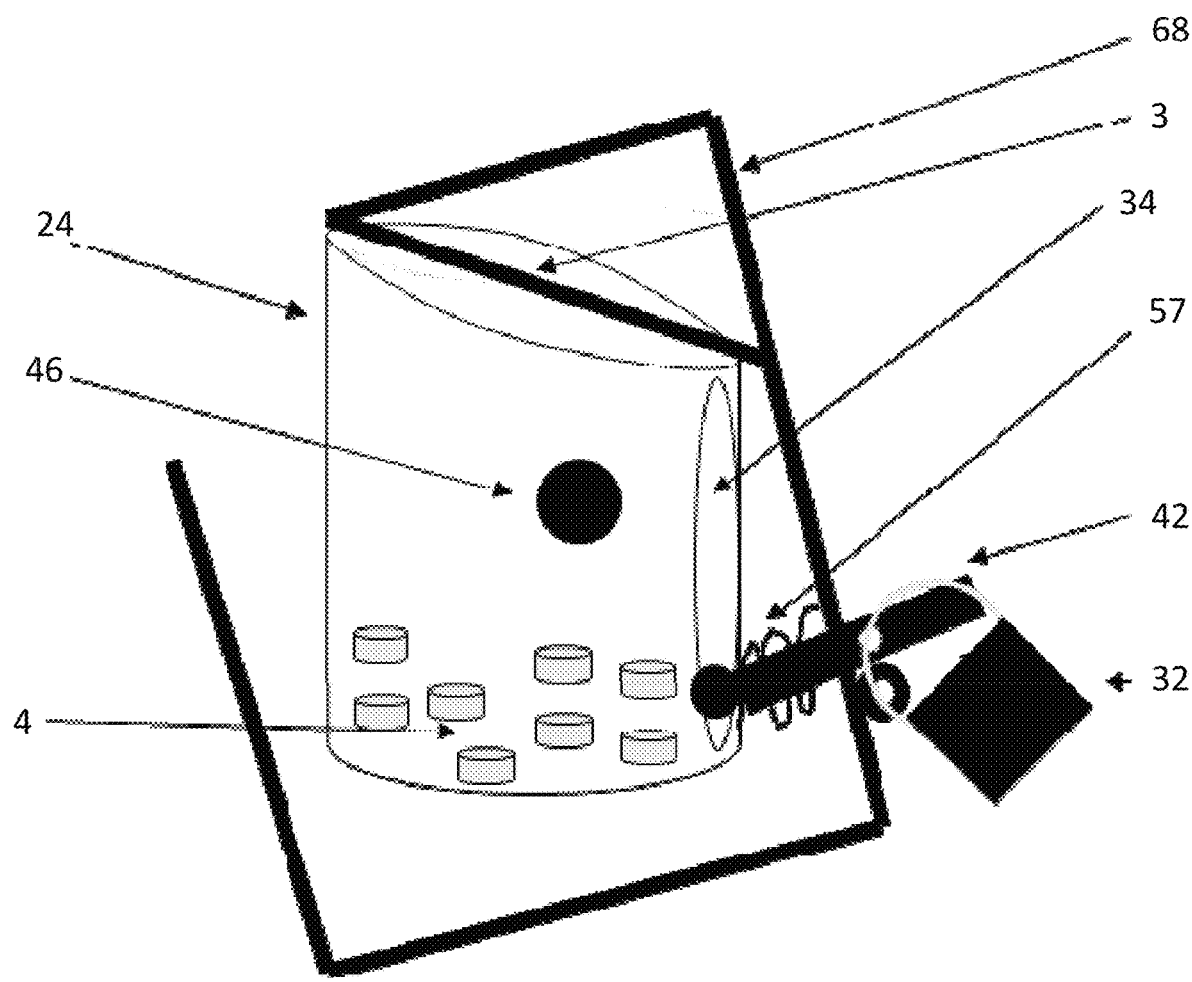
FIG. 8 schematically shows another alternative embodiment of the device in the secured position in accordance with illustrative embodiments of the invention.

FIG. 8 schematically shows an embodiment of the deterrent device with a pharmaceutical bottle in accordance with illustrative embodiments of the invention. Illustrative embodiments have the housing 1, i.e., an inner bottle 24 formed from a pharmaceutically acceptable material such as HDPE, polypropylene, polyethylene terephthalate, high density polyethylene, polyvinyl chloride, polystyrene, and/or polylactide, which can be clear, tinted or opaque. The bottle 66 has a closed bottom, and an open top that is shaped at an angle. The bottle 66 holds a pharmaceutical pill, tablet, capsule, gel cap, powder, or other drug 4 form. The pharmaceutical can be a drug 4 that is prone to abuse such as a hydrocodone, morphine, or oxycodone. Although it should be understood that the pharmaceutical can be any drug 4.

The inner bottle 24 is housed inside the physical deterrent 20. In illustrative embodiments, the physical deterrent may be an outer cylinder 68 formed from a hard material such as polycarbonate. The inner bottle 24 is attached to the outer cylinder 68 by a pivot 46 which allows the inner bottle 24 to partially rotate relative to the outer cylinder 68. The inner bottle 24 has a top that may cut at an angle to be able to seal tightly against an angled portion of the outer cylinder 68. In FIG. 8, the inner bottle 24 is shown sealed against the outer cylinder 68.

The bottle 66 is not allowed to freely pivot by a rod 42. The rod 42 can be attached to either side or the bottom of the bottle 66. The rod 42 can be locked to the cylinder 68 by a lock 32, such as a padlock. When locked, the pharmaceuticals 4 are inaccessible. The rod 42 is anchored to a container 34 that houses one or a combination of a drug antagonist (e.g., naloxone or naltrexone), a bright colorant, an emetic (e.g., ipecac syrup), a foul odor (e.g., pepsin or butanethiol), a gelling agent, an encapsulating agent (e.g., glue), a flushing agent (e.g., niacin), and/or an irritant (e.g., capsaicin). If illustrative embodiments of the invention are forced into the open position (e.g., when in the locked mode), the container 34 ruptures and spills or sprays the abuse deterrent substance on the drug 4. The substance in the container 34 can be brightly colored to clearly indicate when the inner pharmaceutical 4 is sprayed. Alternatively, the substance may have no color.

Illustrative embodiments incorporate a physical abuse deterrent in the hard outer cylinder 68 and inner bottle 24. Illustrative embodiments of the invention also incorporate a chemical abuse deterrent in the form of the deterrent substance held within the container 34. The device can have a spring 70 that automatically closes the device after use.

Figure 9:
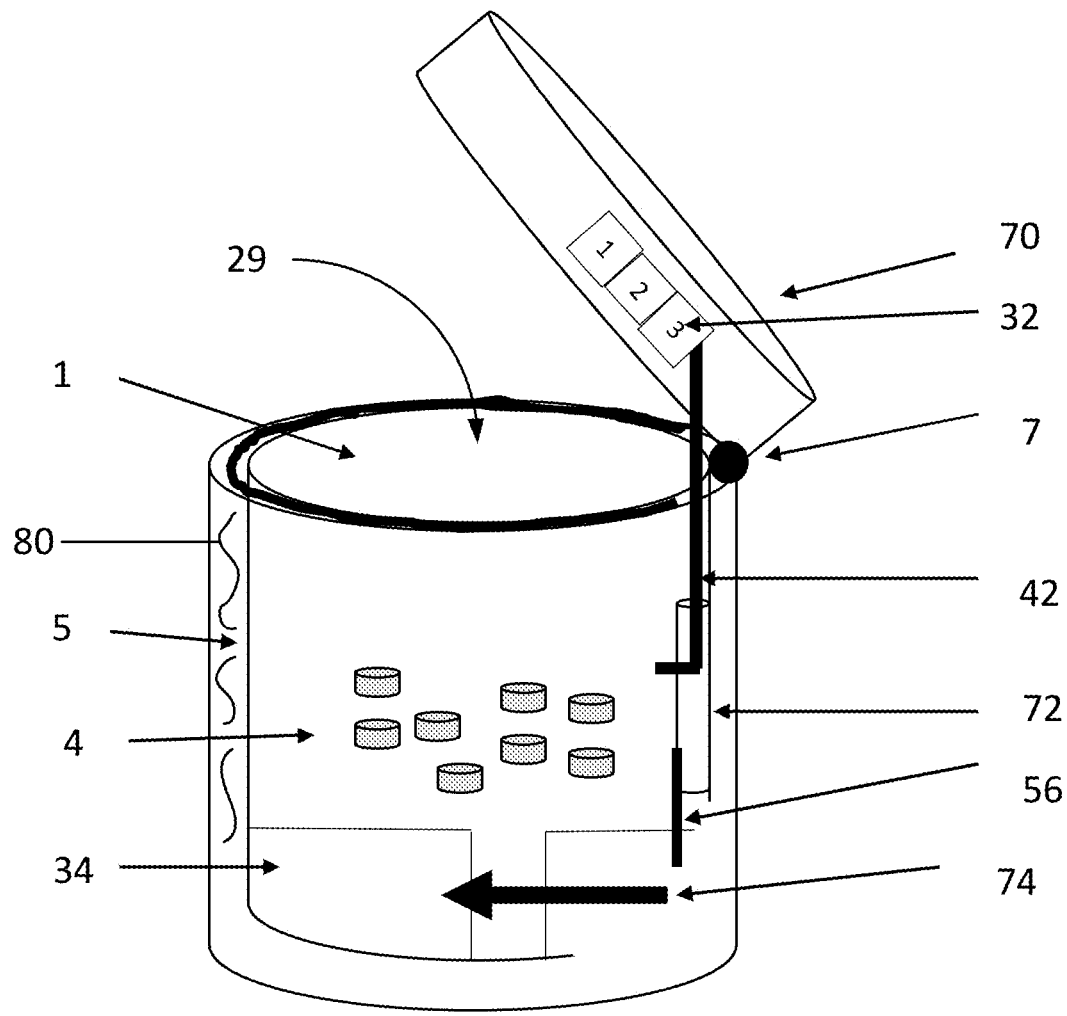
FIG. 9 schematically shows an alternative embodiment of the device that is built-in to the drug housing in accordance with illustrative embodiments of the invention.

FIG. 9 schematically shows an abuse deterrent device 2 that is built-in to the housing 1 in accordance with illustrative embodiments of the invention. The housing 1 may be any container, e.g., a pharmaceutical bottle formed from pharmaceutically acceptable material. The pharmaceutical bottle 1 can be formed from HDPE (high-density polyethylene), polypropylene, polyethylene terephthalate, high density polyethylene, polyvinyl chloride, polystyrene, polylactide, stainless steel, aluminum, and/or glass, and can be clear, tinted, or opaque. As described previously, the bottle may hold a drug 4 therein.

In some embodiments, the walls 5 of the housing 1 may be hollow and filled with pressurized gas (e.g., pressurize air, and/or compressed nitrogen). The drug 4 can properly be accessed through an access port, such as opening 29. If someone improperly tries to access the drug 4 by cutting through the walls 5, or the lid 70, the pressure inside the wall 5 is changed. The change in pressure activates the release of the deterrent. Like many containers that hold drugs 4, the housing 1 has a physical deterrent, such as a lid 70. FIG. 9 schematically shows the physical deterrent 70 in the unsecured position. The lid 70 is attached to the body of the housing 1 by a hinge 7. In some embodiments, the hollows walls 5 and the lid 70 are fluidly connected (e.g., by a tube—not shown) to form a connected uniform pressure. Thus, even if the user cuts through the lid 70, the pressure drop activates the release of the deterrent. Furthermore, in some embodiments there is a reservoir of compressed gas inside the walls 5 to maintain a consistent pressure within the walls over time.

In some embodiments, the wall 5 and/or lid 70 contains a deterrent trigger, such as an electrically conductive matrix (e.g., a matrix of wires 80). If the deterrent trigger is activated (e.g., wires 80 are broken and/or cut), this triggers the release of the plug 74 from the deterrent container 34 (e.g., by a solenoid that releases the plug 74 from the container 34), and the deterrent is positioned (e.g., sprayed) onto the drug 4. Thus, illustrative embodiments release chemical deterrent when the user cuts and/or breaks through the housing 1 and/or the physical deterrent.

The bottle has a security lock 32. The lock 32 in the figure is a rotating combination lock 32. The lock 32 actuates a bent rod 42 in a channel 72. When the lock 32 is in the unlocked mode, the rod 42 moves freely in the channel 72, allowing the lid 70 to open. When the lock 32 is in the locked mode, the rod 42 is trapped by the channel 72, and the lid 70 does not normally open. Forcing the lid 70 open in the locked mode causes the rod 42 to pull on the channel 72, which in turn pulls on the pin 56. In some embodiments, pulling on the pin 56 depressurizes the housing wall 5. Additionally, or alternatively, pulling on the pin 56 may release a plug 74 (e.g., in some embodiments the pin 56 in its resting state may hold the plug 74 in place—or may be attached to the plug 74).

The deterrent container 34 houses a drug antagonist (e.g., naloxone, naltrexone, methylnaltrexone, and nalmefene), a bright colorant, a black colorant (e.g., that makes the drug 4 less visually appealing as well as indicating that the antagonist has deployed), an emetic (e.g., ipecac syrup), a foul odor (e.g., pepsin and/or butanethiol), a gelling agent, an encapsulating agent (e.g., glue), a flushing agent (e.g., niacin), and/or an irritant (e.g., capsaicin). Other useful opioid receptor antagonists are known (see, e.g., Kreek et al., U.S. Pat. No. 4,987,136), a bright colorant, an emetic (e.g., ipecac syrup), a foul odor (e.g., pepsin or butanethiol), a gelling agent, an encapsulating agent (e.g., glue), a flushing agent (e.g., niacin), and/or an irritant (e.g., capsaicin).

The container 34 is normally pressurized such that the plug 74 keeps the deterrent in the container. When the plug 74 is removed from the container 34, the deterrent is positioned (e.g., sprayed) onto the drug 4. In some embodiments, the substance in the container 34 may be colored (e.g., brightly and/or with black colorant) to clearly indicate that the drug 4 has deterrent. A spring may automatically close and lock the device after use.

Figure 10:
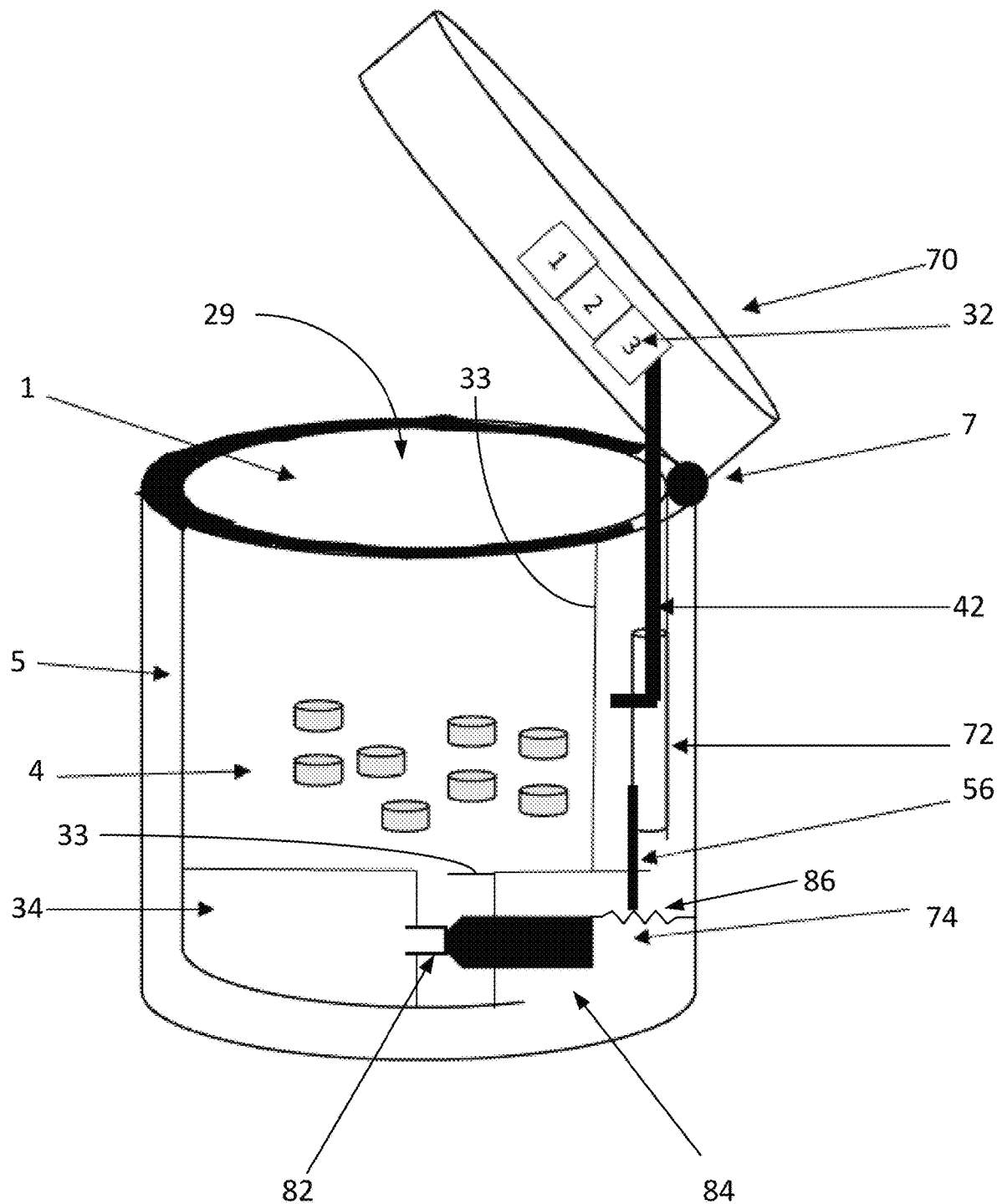
FIG. 10 schematically shows an alternative embodiment of the device that is built-in to the drug housing in accordance with illustrative embodiments of the invention.

FIG. 10 schematically shows an alternative embodiment of the abuse deterrent device 2 that is built-in to the housing 1 in accordance with illustrative embodiments of the invention. The device 2 as shown is incorporated into a pharmaceutical bottle. The housing 1 may be formed from amber polypropylene. It should be understood that the housing may come in a variety of sizes, e.g., as is typical with various pharmaceutical bottle sizes. The drug 4 can properly be accessed through an access port, such as opening 29. Some embodiments may have a partition 33 that blocks or hinders the drug 4 from moving into different parts of the housing 1. FIG. 10 schematically shows the physical deterrent 70 in the unsecured position.

As with the embodiment shown in FIG. 9, the wall 5 may be filled with pressurized air. The housing may include a hinge 7 and/or a lid 70 that are fluidly connected to the wall 5, and also filled with pressurized air. Thus, cutting through any part of the device and/or housing (e.g., the hinge 7, lid 70, or wall 5) activates the release of the chemical deterrent. Furthermore, the container may have the locking mechanism 32 operatively coupled to a rod 42. When the locking mechanism 32 is in the unlocked mode, the rod 42 may be rotated in the channel 72, such that the rod 42 moves freely in the channel 72 without resistance. In the locked mode, the rod 42 is rotated such that it does not move freely in the channel 72 because of interference with the channel 72. Forcing the lid open in the locked mode causes the rod 42 to pull on the channel 72, which also pulls the pin 56 and depressurizes the bottle wall 5.

The deterrent compartment 34 is pressurized, e.g., by containing an opioid antagonist, naltrexone, pepsin for essence, and/or a black colorant in a compressed aerosol foam formulation. In the absence of the plug 74, the pressurized contents in the deterrent compartment 34 are otherwise released/sprayed into the inside of the container and onto the drug 4 through a nozzle 82. To that end, the pressure inside the deterrent compartment 34 may be higher than the pressure inside of the drug 4 container and/or in the pressurized walls 5 of the container. In order for the plug 74 to prevent the accidental discharge of the contents within the deterrent compartment 34, the plug 74 provides sufficient counter pressure on the deterrent compartment 34 (e.g., on the nozzle 82). To that end, the back 84 of the plug 74 may be pressurized by the walls 5 and/or other parts of the housing 1. Under normal circumstances (e.g., when the housing 1 has not been cut open, and the pressure within the wall 5 is maintained) there is sufficient counter pressure provided by the plug 74 such that the deterrent is prevented from escaping the deterrent compartment 34.

In illustrative embodiments, if the housing 1 is improperly breached (e.g., cut open) then the pressure inside the walls 5 drops, and the plug no longer provides sufficient counter pressure to block release of the contents within the deterrent compartment 34. Thus, when the drugs 4 are improperly accessed, the plug 74 stops blocking the release of the contents within the deterrent compartment 34, and the contents are released/sprayed onto the drug 4. Additionally, or alternatively, a spring 86 may provide the counter pressure on the plug 74. In some embodiments, the pin 56 may, for example, remove the counter pressure provided by the spring 86 (e.g., by pulling the spring 86 away from the plug 74). The above described illustrative embodiments are merely exemplary, and not intended to limit various embodiments of the invention. A person of skill in the art can think of numerous other ways through which the release of the deterrent within the deterrent container 34 may be activated (e.g., electronically opening/closing nozzle 82 instead of the plug 84).

A person of skill in the art will be able to modify the device (e.g., shape and or material of the plug 74, shape and or material of the deterrent container 34, stiffness of spring 86, etc.) to prevent the accidental release of the deterrent in the compartment 34 during the normal use of the bottle. Thus, various embodiments may be configured to account for different circumstances that may be encountered normally in use (e.g., if a part of the bottle is accidentally crushed—some embodiments may account for this change in pressure and are configured not to release the deterrent 34 absent a certain threshold reduction in pressure of the walls 5).

Figure 11:
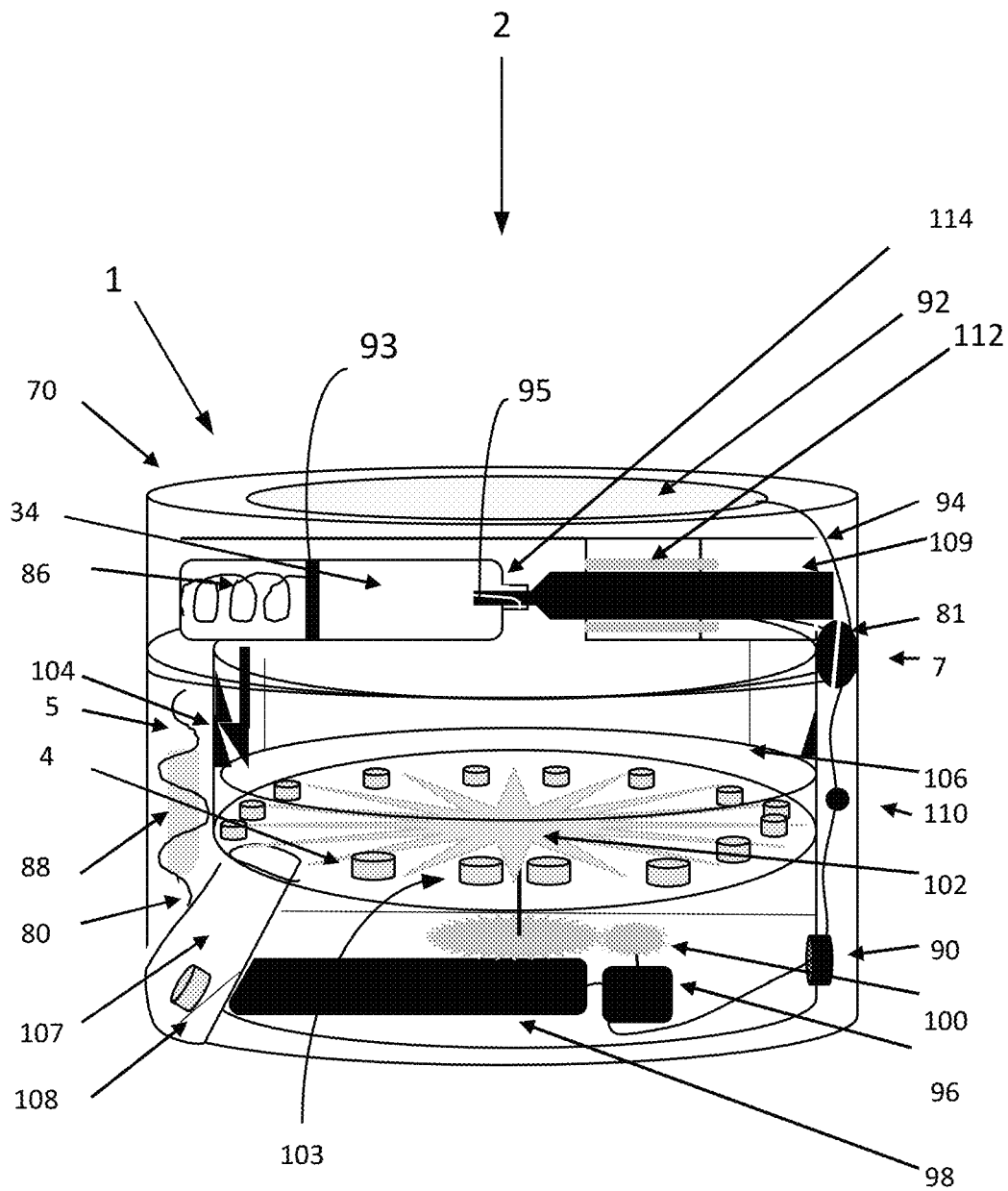
FIG. 11 schematically shows another alternative embodiment of the abuse deterrent device that is built-in to the drug housing in accordance with illustrative embodiments of the invention.

FIG. 11 schematically shows another alternative embodiment of the abuse deterrent device 2 that is built-in to the housing 1 in accordance with illustrative embodiments of the invention. FIG. 11 schematically shows the physical deterrent 70 in the secured position. In this embodiment the abuse deterrent substance is pressurized by a spring 86. Alternatively, or additionally, the abuse deterrent container 34 may be pressurized by gas.

The housing 1 may be any container, e.g., a pharmaceutical bottle formed from pharmaceutically acceptable material. The pharmaceutical bottle 1 can be formed from HDPE (high-density polyethylene), polypropylene, polyethylene terephthalate, high density polyethylene, polyvinyl chloride, polystyrene, polylactide, stainless steel, aluminum, and/or glass, and/or may be clear, tinted, or opaque. As described previously, the bottle may hold the drug 4 therein.

In some embodiments, the walls 5 of the housing 1 may be hollow and filled with pressurized air. In alternative embodiments, the walls may be filled with compressed nitrogen. Compressed nitrogen does not have water vapor in it and may keep the pressure within the walls 5 more steady than pressurized air. It should be understood that a variety of different compressed gases may be used, and that discussion of "air" is merely intended to facilitate discussion of illustrative embodiments, and not to limit them thereby.

The air pressure in the walls 5 pushes against a piston 109. At least a portion of the piston 109 is configured to move from the area of the pressurized bottle walls 5 (e.g., double layer walls) to the unpressurized environment inside the bottle (e.g., where the drugs 4 are). The piston 109 may be sealed with gaskets 112 to prevent pressure from escaping the bottle walls 5 while the piston 109 moves. In the embodiment shown, the tip 114 of the piston 109 presses into the abuse deterrent container 34 and seals it. When the tip 114 backs out of the abuse deterrent container 34, the pressure from the spring 86 pushes the plate 93 in the container 34, and causes the abuse deterrent substance, which is in the container 34, to spray out of the container 34 and down onto the medicine 4.

The tip 114 of the piston 109 may have a channel 95 through which deterrent may be dispensed. When the piston 109 partially backs out of the container 34, the channel 95 directs the abuse deterrent substance onto the medicine 4. Thus, the channel 95 acts as a passageway that directs the deterrent substance towards the medicine 4. In this manner, the pressure within the walls 5 keeps the abuse deterrent substance contained within the deterrent container 34.

If the drug 4 is improperly accessed (e.g., by cutting through the walls 5), the pressure inside the wall 5 changes. The change in pressure activates the release of the deterrent. Like many containers that hold drugs 4, the housing 1 has a lid 70. The lid 70 is attached to the body of the housing 1 by a hinge 7. In some embodiments, the hollows walls 5 and the lid 70 are fluidly connected (e.g., by a tube 81) to form a connected uniform pressure. Thus, even if the user cuts through the lid 70, the pressure drop activates the release of the deterrent. Furthermore, in some embodiments there is a reservoir of compressed gas 100 inside the walls 5 to maintain a consistent pressure within the walls over time. In some embodiments, there may be an adjustable pressure valve 90 that controls the pressure within the walls 5. To that end, a pharmacist who is giving out the medication may pressurize the container at the time of delivery to the patient and/or activate the deterrent system.

In some embodiments, the wall 5 and/or the lid 70 contain an electrically conductive matrix 80, such as a matrix of wires 80. If the wires 80 are broken and/or cut, this triggers a solenoid that pushes the tip 114 of the piston away from the container 34, and the deterrent is positioned (e.g., sprayed) onto the drug 4. Thus, illustrative embodiments release chemical deterrent when the user cuts and/or breaks through the housing 1.

Illustrative embodiments have a touchscreen 92 on the lid, through which the locking mechanism 32 may be accessed. In some embodiments the bottle is operated using simple buttons. The patient enters their code using the touchscreen 92 (for example, the code may be provided or set up by the medical practitioner). The touchscreen 92 thus may control a locking mechanism 32, act as a locking mechanism 32 by having a biometric scanner, it could have reminders and displays that notify the user (e.g., via sound or pop-up notifications), a calendar, and other normal functionalities associated with touch-screens (e.g., such as in a smartphone).

The signal from the touchscreen 92 may be sent through wires 94 to a motor 96 that is powered by a battery 98. The motor causes gears 88 to rotate, which in turn rotates a carousel 102. The carousel 102 has spaces 103 cut into it to accommodate a wide variety of medicine 4 shapes and sizes. In this embodiment the carousel has spaces 103 for 16 dosage units. However, the carousel can have more or less spaces 103. Not all the spaces 103 need to be filled by medicine 4. For example, one space 103 may be left empty so that there is not a drug 4 in the chute 107. Medicine 4 may be placed into the carousel 102 by a physician or pharmacist before the lid 70 is closed. In illustrative embodiments, once the lid 70 is closed, it cannot be opened without causing the abuse deterrent substance 34 to deploy, even if the passcode is correctly entered (e.g., because the passcode rotates the carousel 102—it does not open the lid 70). Furthermore, in some embodiments, there may be multiple tiers of the carousel 102 to facilitate holding more drugs. Illustrative embodiments of the carousel 102 may be porous so as not to prevent the deterrent substance from spraying through the tired carousel.

The lid 70 may be sealed closed by a clasp 104. The bottle may be sealed by a ring 106 that also holds the medicine 4 in place if the bottle is inverted. The ring 106 is porous, so as to not prevent the medicine 4 from being coated by the abuse deterrent substance 34. The carousel 102 can rotate and stop, positioning the medicine over the chute 107. The medicine then drops down the chute 107. The medicine may pass a counter 108. In this embodiment the counter 108 is a gate, however the counter can also be an optical counter. In some embodiments there is a gate and an optical counter that is located under the carousel 102. In some embodiments, the counter 108 only goes one-way, so as to prevent a user from trying to access the drug through the chute 107. In some embodiments, a sensor is connected to the chute 107 and to the valve 90, so that tampering with the chute 107 activates release of the deterrent (e.g., by opening the valve 90 and dropping the pressure in the walls 5).

The bottle can be programmed by the physician or pharmacist to only dispense medication 4 at certain intervals. The bottle can also be programmed to provide reminders to take medication 4. The bottle can also be programmed to deploy the abuse deterrent substance after a certain interval, for example after a week, or after a month, of after six months. The timed deployment of the abuse deterrent substance removes the useful opioid from circulation, and thereby prevents an excess of unused opioid that could lead to misuse or abuse.

The device 2 may have a processor (not shown) that may control the valve 90. For example, the processor may be a part of the touchscreen 92. When the valve 90 is opened, the bottle walls 5 lose pressure, the abuse deterrent substance 34 is sprayed onto the drug 4. In some embodiments, the valve may open automatically at a week, month, three-months, six-months, and/or at the expiration of the medicine 4. Manipulation of the chute 107, the counter 108, and/or the carousel 102, may cause the valve 90 to open.

In alternative embodiments, the walls 5 may contain a conductive wire matrix (in addition to, or instead of, pressurized air), a solenoid may cause the abuse deterrent substance to deploy if a wire 80 is cut. In some embodiments, the walls may be pressurized and include an electrical matrix, thus, the bottle may have a pressure sensor 110 to monitor the pressure within the walls. The bottle walls 5 may be formed in part or in whole from a material that is porous, to allow a precisely controlled release of pressure. This precise release of pressure can cause the abuse deterrent substance to deploy after a predetermined period of time even if the electronics fail (e.g., after 1 month, or six months).

In some embodiments, the lock 32 is a biometric scanner such as a fingerprint scanner. Accordingly, the lock 32 does not open unless the fingerprint which has been programmed is pressed against the lock. The lock 32 can also incorporate a timer that is set to the expiration date of the contained medicine, or to a set interval of a treatment period assigned by a health care worker. As an illustrative example the timer could be set to lock the bottle after a 7 day course of pain medicine is complete.

In some embodiments, the device 2 may be coupled to a dosage counter. Depending on the type of drug 4, the dosage counter may be configured to count the dosage in number of pills, milliliters of fluid, and/or milligrams of drug that is released from the housing 1. After a threshold of dosage has been reached, the dosage counter may be configured to activate the locking mechanism. Furthermore, in some embodiments, an actuator may be coupled to the dosage counter and may cause the physical deterrent to move to the secured position.

Additionally, or alternatively, a dosing scheduler may be coupled to the locking mechanism and/or physical deterrent. The dosing scheduler may control the locking mechanism to unlock only during certain times of the day (e.g., for 30 minutes, between 9 AM and 10 AM, once every other day, etc.).

The device 2 may be network enabled (e.g., Wi-Fi), to receive updates from medical staff (e.g., prescribing doctor) regarding the amount and timing of drug to be released. Additionally, the device may forward data to the doctor regarding the timing and dosage of drug accessed. In some embodiments, the device 2 has network connectivity capabilities and can communicate with an external site and provide information or receive information. In some other embodiments, the device 2 may have an electronic display which may be a touchscreen. The device 2 may also incorporate audible, visual, vibratory or other types of alerts and reminders for the patient 8.

Although the above discussion discloses various exemplary embodiments of the invention, it should be apparent that those skilled in the art can make various modifications that will achieve some of the advantages of the invention without departing from the true scope of the invention.

What is claimed is:

1. A device for deterring drug abuse, the device comprising:
- a housing configured to contain a drug that can be accessed through an access port of the housing;
- a physical deterrent configured to move from an unsecured position, wherein the access port of the housing is normally accessible, to a secure position, wherein the access port of the housing is normally inaccessible;
- a locking mechanism coupled with the physical deterrent, the locking mechanism having a locked mode, wherein the physical deterrent is not normally able to move from the secure position to the unsecured position, and an unlocked mode, wherein the physical deterrent is normally able to move from the secured position to the unsecured position;
- a rod that connects the housing and the physical deterrent, the rod being normally movable in the unlocked mode, to allow the physical deterrent to move from the secure position to the unsecure position, the rod further being normally immobile in the locked mode to prevent the physical deterrent from moving from the secure position to the unsecure position, the movement of the rod changing the orientation of the housing relative to the physical deterrent;
- the locking mechanism further coupled with a deterrent container having a deterrent substance therein, such that moving the physical deterrent relative to the housing when the locking mechanism is in the locked mode activates the release of the deterrent substance to the drug.

2. The device as defined by claim 1, wherein the physical deterrent is oriented relative to the housing in such a way as to prevent and/or significantly hinder access to the access port when in the locked mode, and the physical deterrent is oriented relative to the housing in such a way to allow access to the access port when in the unlocked mode.

3. The device as defined by claim 1, wherein the housing is rotatable relative to the physical deterrent in the unlocked mode, and the housing is not rotatable relative to the physical deterrent in the locked mode.

4. The device as defined by claim 1, wherein the housing is an IV fluid bag, a vial, a syringe, a canister, or a bottle.

5. The device as defined by claim 1, wherein the deterrent substance is a drug antagonist, a chemical irritant, a gelling agent, a colorant, an emetic, and/or an encapsulating agent.

6. The device as defined by claim 1, wherein the deterrent substance has a foul odor.

7. The device as defined by claim 1, wherein the locking mechanism includes a padlock, and/or a combination lock.

8. The device as defined by claim 7, further comprising an electrically conductive matrix within the walls of the housing.

9. The device as defined by claim 1, wherein the deterrent substance is released when the access port is opened in the locked mode.

10. The device as defined by claim 1, wherein the physical deterrent is external to the housing.

11. The device as defined by claim 1, wherein cutting a wall of the housing releases the deterrent substance.

12. The device as defined by claim 1, wherein the housing has hollow walls filled with pressurized air.

13. A method of accessing a drug provided inside a housing having a physical deterrent and a chemical deterrent, the method comprising:
- providing:
  - a housing configured to contain a drug, the housing having an access port through which the drug can be accessed,
  - a movable physical deterrent that blocks the access port of the housing when the physical deterrent is in a secure position,
  - a locking mechanism that, in a locked mode, prevents and/or significantly hinders the physical deterrent from moving from the secure position to an unsecured position, wherein the physical deterrent no longer blocks the access port in the unsecured position,
  - a moveable rod that connects the housing and the physical deterrent, the rod capable of moving when the locking mechanism is in an unlocked mode to allow the physical deterrent to move from the secure position to the unsecured position, and
  - a deterrent container configured to hold a deterrent substance therein that is released when the drug is accessed while the physical deterrent is in the secure position and the locking mechanism is in the locked mode;
- unlocking the locking mechanism;
- moving the physical deterrent into the unsecure position; and
- accessing the drug.

* * * * *